(12) United States Patent
Scheer et al.

(10) Patent No.: US 6,746,585 B2
(45) Date of Patent: Jun. 8, 2004

(54) GAS SENSOR, ESPECIALLY A LAMBDA PROBE

(75) Inventors: Heiner Scheer, Berghuelen (DE); Hans-Joerg Renz, Leinfelden-Echterdingen (DE); Johann Riegel, Bietigheim-Bissingen (DE); Lothar Diehl, Stuttgart (DE); Sabine Thiemann-Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/110,906

(22) PCT Filed: Aug. 16, 2001

(86) PCT No.: PCT/DE01/03150
§ 371 (c)(1),
(2), (4) Date: Jul. 25, 2002

(87) PCT Pub. No.: WO02/14660
PCT Pub. Date: Feb. 21, 2002

(65) Prior Publication Data
US 2003/0019279 A1 Jan. 30, 2003

(30) Foreign Application Priority Data
Aug. 18, 2000 (DE) .......................................... 100 40 505

(51) Int. Cl.[7] ....................... G01N 27/409; G01N 27/41

(52) U.S. Cl. ................ 204/425; 204/426; 204/427
(58) Field of Search .................................. 204/421–424

(56) References Cited

U.S. PATENT DOCUMENTS

| 4,732,663 | A | * | 3/1988 | Kato et al. |
| 4,798,693 | A | * | 1/1989 | Mase et al. |
| 4,824,549 | A | * | 4/1989 | Hamada et al. |
| 4,880,519 | A | * | 11/1989 | Wang et al. |
| 5,169,512 | A | | 12/1992 | Wiedenmann et al. |
| 5,314,604 | A | | 5/1994 | Friese et al. |
| 5,421,984 | A | | 6/1995 | Saito et al. |

FOREIGN PATENT DOCUMENTS

| DE | 37 44 206 | 8/1988 |
| DE | 44 01 749 | 7/1994 |

* cited by examiner

Primary Examiner—Kaj K. Olsen
(74) Attorney, Agent, or Firm—Kenyon & Kenyon

(57) ABSTRACT

A gas sensor has improved electrical properties. In the top view of the layer planes of the body of the sensor, printed circuit traces for electrodes are arranged outside of cavities in the body, e.g., outside of the reference air duct. Furthermore, the electrodes are enlarged in the direction of the exhaust-side end of the sensor. Also, the printed circuit traces have an increased layer thickness or are formed as a double layer.

19 Claims, 2 Drawing Sheets

GAS SENSOR, ESPECIALLY A LAMBDA PROBE

FIELD OF THE INVENTION

The present invention relates to gas sensors, e.g., lambda probes, including a body formed as a sintered ceramic laminate and a reference air duct situated therein within a layer of the laminate, an electrical resistance heater provided on its one side and an electrode configuration provided on its other side, the electrode configuration including at least one reference electrode that:is arranged on the inside of a boundary wall of the reference air duct and is permeable for gases at least regionally and that includes a Nernst electrode that is acted upon by gases to be sensed, the Nernst electrode is also at least regionally permeable for gases and separate from the reference electrode by a solid electrolyte layer that is conductive and permeable for ions, e.g., oxygen ions, and the electrodes connected to printed circuit traces that essentially extend in the direction of the reference air duct.

BACKGROUND INFORMATION

Exhaust systems of modern internal combustion engines, particularly for motor vehicles, are regularly provided with catalytic converters for converting harmful exhaust gases into harmless reaction products. In order for the catalytic converters to function well, it is necessary to feed air and fuel to the engine in a predefined proportion. The engine controls provided for this purpose are connected on their input side to a so-called lambda probe the signals of which represent the composition of the exhaust gas and, thus, enable the engine control to adjust the ratio of fuel and combustion air in a manner optimal for the catalytic converter.

Two configurations are conventional in this connection.

In the one configuration, stoichiometric combustion is targeted, i.e., the oxygen quantity in the combustion air corresponds exactly to the oxygen requirement for complete combustion of the supplied fuel. Therefore, the engine is operated using neither an excess of oxygen ($\lambda>1$) nor using a deficiency of oxygen ($\lambda>1$). This operating method may, therefore, by characterized by $\lambda=1$.

When sensing exhaust gas,: narrow-band lambda probes where the Nernst electrode is acted upon by the exhaust gas as directly as possible are sufficient for this stoichiometric combustion.

In this instance, the effect is used by the engine control that an electrical voltage able to be tapped off between the reference electrode and the Nernst electrode and generated by diffusion of oxygen ions significantly changes its value in the vicinity of $\lambda=1$, and a signal is consequently available that clearly displays a deviation from the desired operating mode using stoichiometric combustion in the direction of an operating mode having an oxygen deficiency as well as in the direction of an operating mode having an oxygen excess.

Such sensors are described in German Published Patent Application No. 44 01 749, for example.

In the other configuration, the objective is predominant operation of the internal combustion engine with an oxygen excess during combustion since the fuel consumption is able to be noticeably reduced as a result. However, during combustion using an oxygen excess, harmful nitrogen oxides are produced that may only be absorbed for a limited time by so-called adsorption catalysts in the exhaust branch of the motor vehicle. In each case prior to exhausting the absorption capacity of the adsorption catalysts, the engine operation must be switched over briefly to combustion with an oxygen deficiency in order for the incompletely combusted fuel components now entering the exhaust branch to be able to reduce the nitrogen oxides previously stored in the catalytic converter to nitrogen. In this instance, the engine control, i.e., the internal combustion engine, must be constantly switched at intervals between an operating mode that is predominant with respect to time and in which the values of $\lambda$ are greater than 1 and a relatively brief operating mode in which the values of $\lambda$ are less than 1.

Broadband lambda probes are necessary for such an intermittent operating mode having drastically changing values of $\lambda$.

In the case of such lambda probes, the Nernst electrode is arranged at a separate chamber that communicates with the exhaust-gas stream via a diffusion path arranged in the body of the probe. Arranged within this chamber is also an internal pump electrode that may be electrically connected to the Nernst electrode and also cooperates through a solid electrolyte layer with an external pump electrode that is exposed to the exhaust-gas stream as directly as possible. If an external electrical voltage is applied between the two pump electrodes, which are both configured to be permeable for gases at least regionally, an oxygen ion current the direction of which depends on the polarity of the applied voltage and the intensity if which is determined by the electrical voltage difference as well as by the difference in the oxygen concentration at the pump electrodes is generated between the pump electrodes. This oxygen ion current accordingly controls the diffusion current of the exhaust gases in the diffusion chamber. The external electrical voltage between the pump electrodes and the electrical current occurring between the pump electrodes due to the oxygen ion current are adjusted by a controller so that an electrical voltage having a predefined setpoint value is always maintained between the reference electrode and the Nernst electrode. As such, the polarity and intensity of the electrical current occurring between the pump electrodes are a signal that correlates to the composition of the exhaust gases and, thus, to the $\lambda$ values.

Such probes are described in German Published Patent Application No. 37 44 206, for example.

Aging processes such as pollution change the properties of the aforementioned gas sensors.

SUMMARY

In accordance with the present invention, it is provided that in a top view of the layer planes of the laminate, the printed circuit traces corresponding to the electrodes are arranged at least partially next to the reference air duct.

This may be applicable for the printed circuit traces of the pump electrodes.

The present invention is based on using the pressing pressure exerted during and/or prior to sintering the probe body to the laminate for compressing the composite structure of the printed circuit traces and in this connection to effectively increase the pressure forces exerted on the printed circuit traces by arranging the printed circuit traces in the laminate without being covered by hollow spaces as viewed from above. Consequently, a smaller electrical resistance of the printed circuit traces as well as a higher durability of the printed circuit traces with respect to aging effects is achieved with the result that the change in the electrical properties of the probe in the case of increasing age are significantly reduced.

In addition or alternatively, further measures may be provided. For example, the internal and/or external pump electrode may have a surface that is larger than the base plan of the gas chamber arranged between the Nernst electrode and the internal pump electrode.

The pump electrodes on a region diametrically opposed to the corresponding printed circuit trace, i.e., in the direction of the top end of the probe body, may extend beyond the base plan of the gas chamber.

Furthermore, it may be advantageous for constant electrical properties when the printed circuit traces have a comparably large layer thickness. For this purpose, the printed circuit traces may be produced using printing technology with relatively wide-meshed screens (e.g., screens including a 250 mesh). Moreover, the printed circuit traces may also be printed as a double-layer.

Finally, the pressure material for the printed circuit traces may have a high proportion of electrically conductive particles, e.g., based on platinum.

Example embodiments of the lambda probe according to the present invention are explained in greater detail below and are illustrated in the drawings.

DETAILED DESCRIPTION

Figure 1:
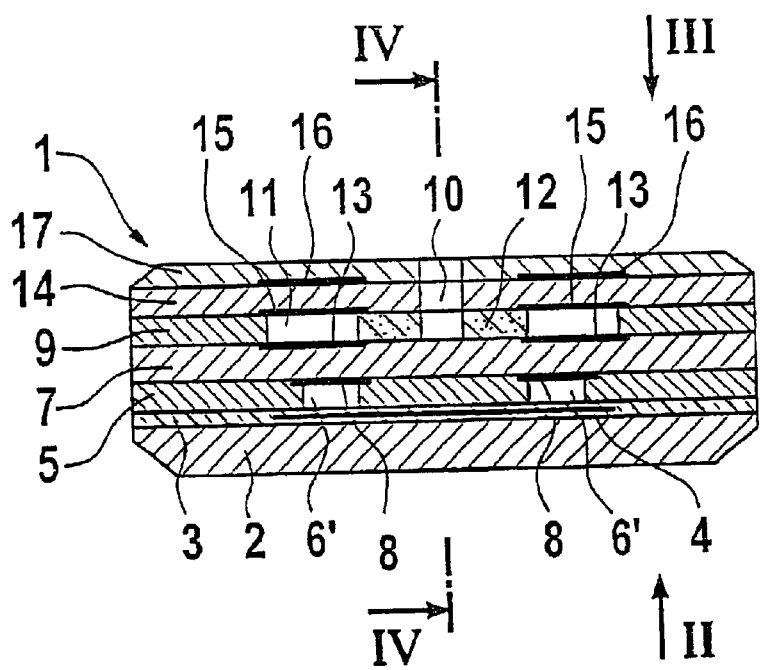
FIG. 1 is a cross-sectional view of a broadband lambda probe corresponding to line of intersection I—I illustrated in FIG. 2 and FIG. 3 in the region of the top end of the probe body projecting into the exhaust-gas stream.

As illustrated in FIG. 1, the lambda probe includes a body 1, which is formed as a ceramic laminate. The layers of the laminate are placed or deposited on one another in the green condition. Subsequent sintering, which may be performed after or during simultaneous pressing of the laminate, produces a hard ceramic body 1.

In the example embodiment illustrated in FIG. 1, a bottom layer 2 is provided in the form of a thicker film of zirconium oxide. Above this is an electrically insulating double layer 3, in which an electrical resistance heater 4 as well as corresponding printed circuit traces for electrical current supply are embedded. Above that is layer 5, which is produced and patterned by screen printing and is made, for example, of a zirconium oxide paste. Recessed within this layer is a reference air duct 6, the base plan of which is illustrated by manner of example in FIG. 2 and is explained in greater detail below. As illustrated, this reference air duct 6 may have two end regions 6', which communicate with one another, in the area of the sectional plane illustrated in FIG. 1.

In some instances, layer 5 may also be formed by a film in which duct 6 is punched out.

Above layer 5 is a solid electrolyte layer 7, e.g., in the form of a film made of zirconium oxide to which yttrium oxide is added. A gas-permeable, layered reference electrode 8 of a porous platinum material, which is connected via a layered printed circuit trace 8' connected thereto (see FIG. 2) to a connection contact on body 1 explained below, is arranged on the side of layer 7 facing reference air duct 6, i.e., between layers 5 and 7, at least in the area of end regions 6' of reference air duct 6.

Above solid electrolyte layer 8 is a thin layer 9, which is patterned using printing technology and is in turn produced from a zirconium oxide paste, for example. This layer 9 includes a large recess that is arranged centrically to an exhaust-gas access hole 10, which extends through body 1 perpendicularly to its layers. Porous material 12 is deposited within the indicated recess while leaving open a ring space 11. As illustrated, access hole 10 may be configured as a blind hole or as an opening passing completely through body 1.

In the region of annular space 11, solid electrolyte layer 7 supports a gas-permeable, layered Nernst electrode 13 of a porous platinum material.

Another solid electrolyte layer 14, e.g., in the form of a film made of zirconium oxide to which yttrium oxide is added, is above layer 9 and porous material 12. This layer 14 supports on it side facing annular space 11 as well as on its side away from annular space 11 gas-permeable, internal and external pump electrodes 15 and 16 made of an at least regionally porous platinum material, these electrodes 15 and 16 are formed such that in a top view of the layers of body 1, they at least essentially cover annular space 11. A gas-permeable protective layer 17 is above layer 14.

In some instances, a positive image of reference air duct 6 as well as of its end pieces 6' and orifices 6" may also be imprinted on layer 7 using a material that is disintegrated or burned off when sintering body 1 or forms a porous, effectively gas-permeable structure.

In general, it may be possible to print layer 3 in a mirror image to layer 7 using the material of layer 5 and, in some instances, also using the material provided for the positive image of reference air duct 6 and it parts 6' and 6". In this manner, layer 5 is able to be produced with a greater thickness.

The previously described lambda probe functions as follows:

The end of body 1 including exhaust-gas access hole 10 is arranged in the exhaust-gas stream or in a region communicating with the exhaust-gas stream of an internal combustion engine, while the other end of body 1 is acted upon by reference air typically from the atmosphere.

Reference air reaches end pieces 6' of the reference air duct via reference air duct 6 and its orifices 6". Via exhaust-gas access hole 10, exhaust gas reaches porous material 12, through which the exhaust gas diffuses into annular space 11.

When the exhaust gas-side end of body 1 is sufficiently heated by electrical resistance heater 4, an electrical voltage, the magnitude of which depends on the partial oxygen pressures within end pieces 6' of the reference air duct as well as within annular space 11, is able to be tapped off between reference electrode 8 and Nernst electrode 13 and consequently between plated through-holes 19 and 20. In this context, the effect is taken advantage of that solid electrolyte layer 7 conducts oxygen ions and the platinum material of aforementioned electrodes 8 and 13 promotes or enables the formation of these oxygen ions with the result that an electrical potential difference that is dependent on the partial oxygen pressure at electrodes 8 and 13 and results in a corresponding ion migration occurs in solid electrolyte layer 7. This potential difference is also referred to as the Nernst voltage.

The partial oxygen pressure in annular space 11 is able to be controlled in that an external electrical voltage having controllable polarity is applied between pump electrodes 15 and 16. The corresponding voltage source is connected to plated through-holes or contacts that are electrically connected to pump electrodes 15 and 16.

In this instance, the effect is in turn used that the platinum material of electrodes 15 and 16 results in the formation of oxygen ions and an oxygen ion current flowing through solid electrolyte layer 14 and having an intensity and direction dependent on the electrical voltage and its polarity is then produced by the external electrical voltage between electrodes 15 and 16. Thus, an electrical signal is able to be tapped off between pump electrodes 15 and 16, e.g., is able to be determined by ascertaining the voltage and current intensity of the electrical resistance of the electric circuit leading across the pump electrodes.

The electrical voltage and consequently also the electrical current between pump electrodes 15 and 16 are controlled by a controller such that electrical voltage able to be tapped off between reference electrode 8 and Nernst electrode 13 and consequently the partial oxygen pressure in annular space 11 always correspond to a defined setpoint value. Therefore, the electrical current able to be tapped off between pump electrodes 15 and 16 is a measure of the oxygen content of the exhaust gas relative to the reference air.

When external pump electrode 16 is at an electrically positive potential with respect to internal pump electrode 15, operating conditions where $\lambda>1$ exist. In the case of a reverse polarity, operating conditions of $\lambda<1$ exist, the magnitude of the electrical resistance between electrodes 15 and 16 correlating to the magnitude of $\lambda$.

The values of $\lambda$ may be acquired in a large value range.

Figure 3:
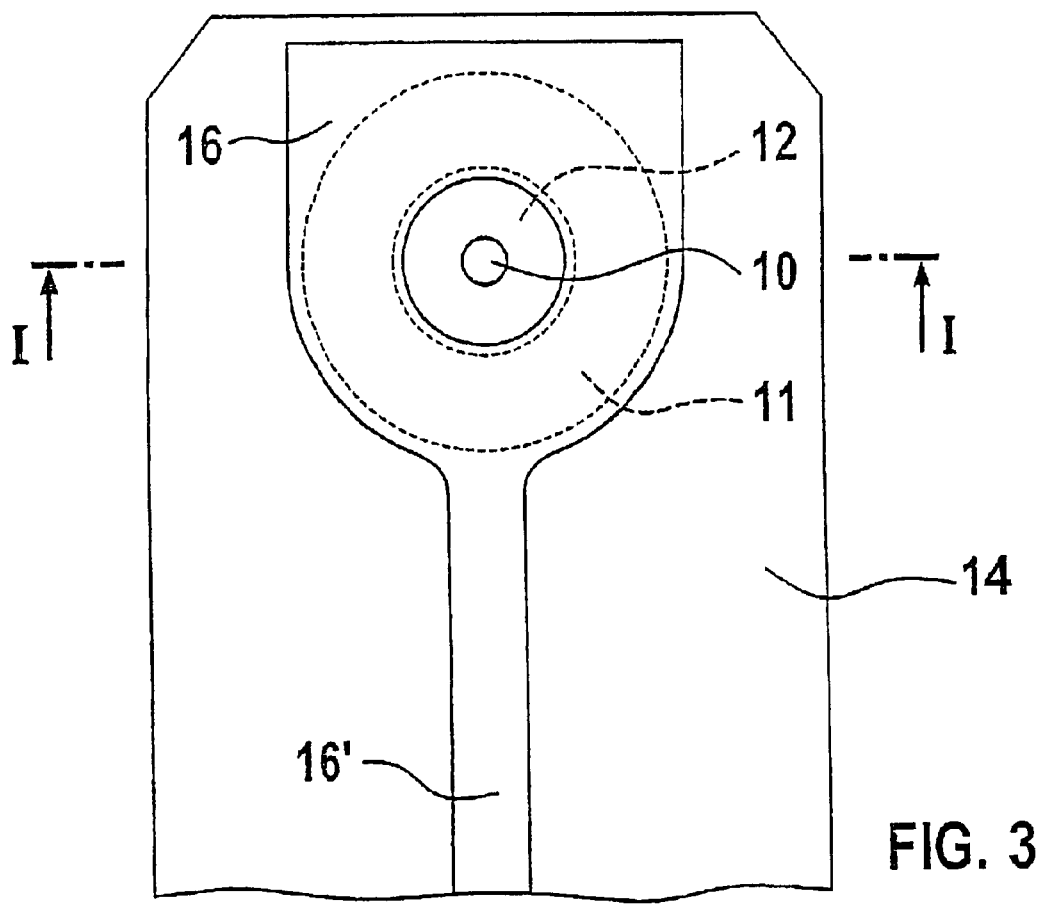
FIG. 3 is a top view corresponding to arrow III illustrated in FIG. 1 of different layers of the laminate including electrodes as well as corresponding printed circuit traces.

In the case of the narrow-band lambda probe, external protective layer 17 is above Nernst electrode 13, i.e., layers 9 and 14 as well as pump electrodes 15 and 16 may not be necessary in comparison with the arrangements illustrated in FIGS. 1 and 3. Given a known and constant partial oxygen pressure, the electrical voltage able to be tapped off between electrodes 8 and 13 is a measure of the partial oxygen pressure of the exhaust gases.

Figure 2:
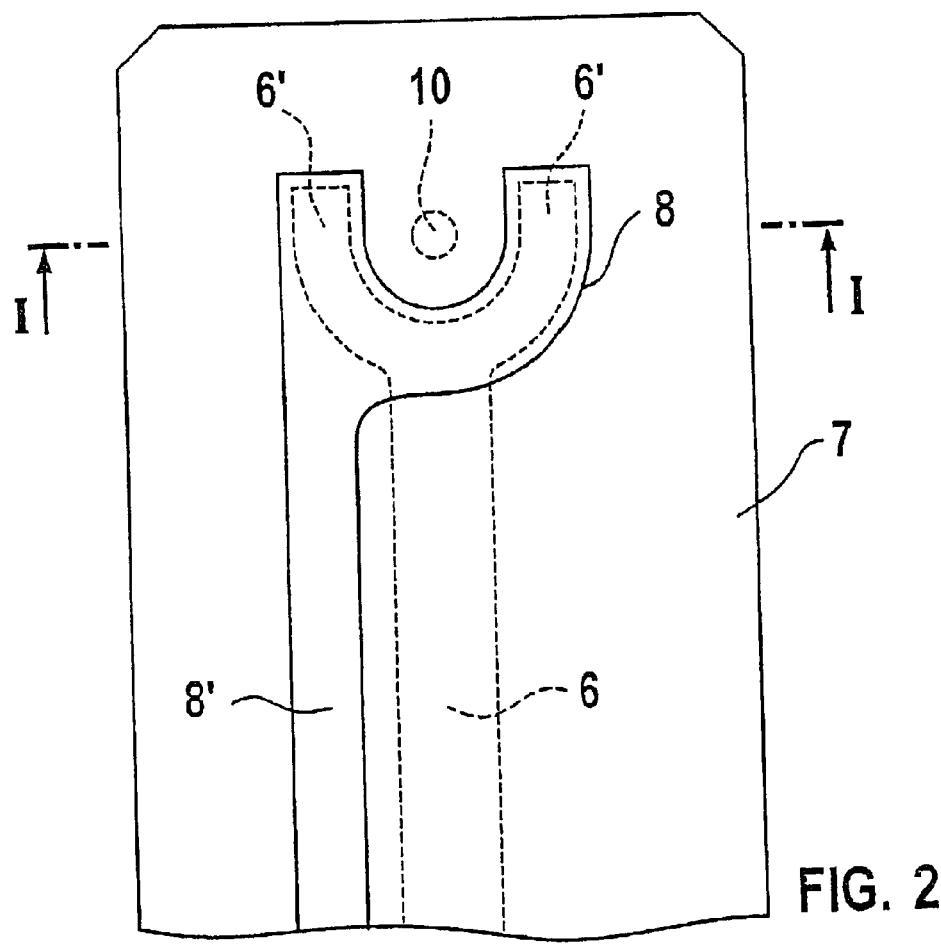
FIG. 2 is a top view corresponding to arrow II illustrated in FIG. 1 of solid electrolyte layer.

FIG. 2 is a top view corresponding to arrow II illustrated in FIG. 1 of solid electrolyte layer 7. Reference electrode 8 as well as a printed circuit trace 8' connected thereto are imprinted on the side of this layer 7 illustrated in FIG. 2. This printed circuit trace 8' leads to a plated through-hole, which is able to extend, for example, through layer 7 as well as the layers above layer 7 illustrated in FIG. 1 and to electrically connect printed circuit trace 8' to a contact tag arranged externally on body 1 on its reference air-side end.

Furthermore, a dashed line illustrated in FIG. 2 represents the position of reference air duct 6 including its ends 6' arranged in the region of reference electrode 8.

As illustrated in FIG. 2, printed circuit trace 8' is outside of reference air duct 6. Consequently, printed circuit trace 8' is subjected to an increased pressing pressure when the laminate of body 1 is pressed prior to and/or during sintering in order to ensure good cohesion of the layers of the laminate.

While reduced pressing pressures occur during this pressing above and/or below reference air duct 6 because almost no forces are able to be applied over the hollow space of duct 6, a high pressure may always be ensured in regions next to reference air duct 6 because in this instance there are no considerable cavities in the laminate.

The aforementioned increase in pressing pressure at printed circuit trace 8' is especially effective when reference air duct 6 is produced within a film-like layer 5 by punching.

It may also be provided that instead of fork-shaped end regions 6' of the reference air duct, only one single end piece enlarged in some instances with respect to the rest of reference air duct 6 be arranged below gas access opening 10, which in this case may be configured as a blind hole in order to be able to ensure a separation from reference air duct 6. Reference electrode 8 has a form similar to the aforementioned end piece of the reference air duct such that reference electrode 8 covers the aforementioned end piece of reference air duct 6 with more or less excess.

FIG. 3 is a top view of solid electrolyte layer 14 corresponding to arrow III illustrated in FIG. 1. Dotted lines represent the position of annular space 11 as well as of porous material 12 via which annular space 11 communicates with gas access hole 10.

External pump electrode 16 is imprinted on the side of solid electrolyte layer 14 illustrated in FIG. 3. It has an ring-shaped configuration similar to the ring shape of annular space 11. However, external pump electrode 16 may be significantly enlarged, e.g., in the direction of the exhaust-side end of layer 14 and also may project in the direction of the longitudinal sides of layer 14 beyond the borders of annular space 11.

As a result of this configuration, a good pump effect is able to be achieved already at a low voltage between pump electrodes 15 and 16, it may be ensured at the same time that a clear proportionality results between the lambda values and the pump current.

Internal pump electrode 15 may have a shape similar to external pump electrode 16.

Moreover, it may be provided for porous material 12 to be arranged in regions adjacent to large-area zones of internal and external pump electrodes 15, 16, respectively, having a narrower width in the radial direction to gas access opening 10. In this manner, the gas access to annular chamber 11 in zones in which pump electrodes 15 and 16 have an increased pump effect is made easier.

It may be provided for all electrodes to configure the corresponding printed circuit traces with good electrical conductivity.

For example, this may be achieved in that the material used for printing the printed circuit traces includes an increased platinum content or an increased content of other effectively electrically conductive particles. While the electrodes may be permeable for gas and are therefore produced using printing technology with a particle mixture that, during sintering, forms an electrically conductive layer that is permeable for gases and ions, gas permeability may not need to be ensured for the printed circuit traces. Accordingly, the metal content of the material of the printed circuit traces may be increased. For example, the electrode material may contain a high proportion of zirconium oxide in comparison with the platinum content, while the material of the corresponding printed circuit traces includes a low zirconium oxide content in comparison with the platinum proportion.

A further possibility for increasing the electrical conductivity of the printed circuit traces is to provide an increased layer thickness of the printed circuit traces. This may be achieved, for example, in that the printed circuit traces are produced by screen printing using comparably wide-meshed nets.

Furthermore, there is the possibility of producing printed circuit traces in each case as a double layer, i.e., two conductive layers may be arranged or printed one above the other.

Figure 4:
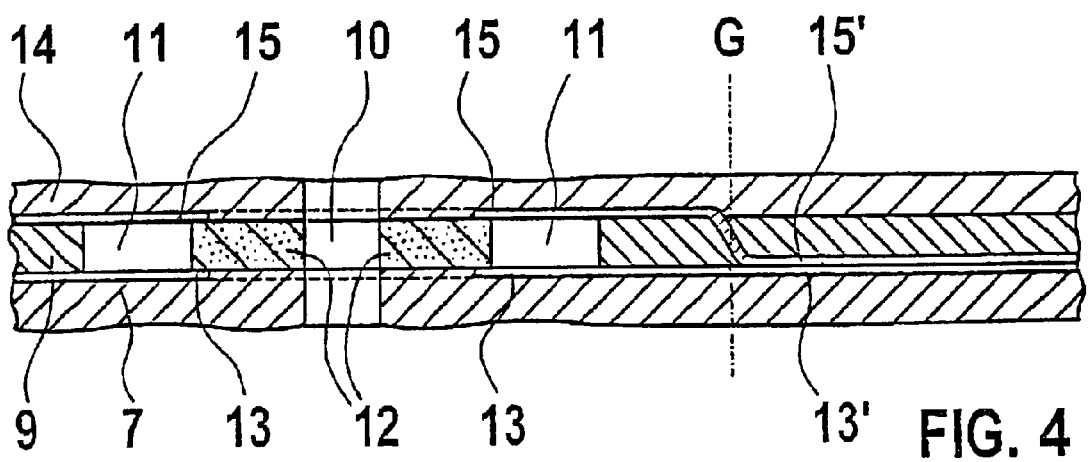
FIG. 4 is a longitudinal cross-sectional view of part of the probe corresponding to line of intersection IV—IV illustrated in FIG. 1.

FIG. 4 is a longitudinal cross-sectional view corresponding to line of intersection IV—IV illustrated in FIG. 2 through layers 7, 9, and 14.

Nernst electrode 13, which is arranged on layer 9 and above chamber 11 and the form of which may be similar to pump electrodes 15 and 16 as viewed from above, includes an assigned printed circuit trace 13', which borders layer 9 and is coincident with printed circuit trace 15' of internal pump electrode 15, so that printed circuit traces 15' and 13' form a double layer.

To enable such a configuration, layer 14 may first be coated on its bottom side illustrated in FIG. 4 only right of a border G with the material of layer 9. Electrode 15 and corresponding printed circuit trace 15' are subsequently printed, and a connection between printed circuit trace 15' on layer 9 and electrode 15 on layer 14 is automatically created in the region of border G.

Porous material 12 as well as the still missing part of layer 9 are then imprinted or superposed on layer 14.

Pump electrode 13 as well as corresponding printed circuit trace 13' may be imprinted on layer 7, which is subsequently placed on layer 9, and printed circuit traces 15' and 13' are sintered together when the laminate is later sintered.

Deviating from the arrangements illustrated in FIG. 3 and 4, e.g., when reference air duct 6 is produced within layer 5 by punching, printed circuit traces (e.g., 13', 15', 16') of all electrodes are arranged off-center on the appropriate layers of the laminate such that, in the top view of the layer planes, no covering by reference air duct 6 is able to occur, and pressing the laminate makes it possible to compact the material of the printed circuit traces effectively while improving the electrical conductivity as was explained above by manner of example with reference to FIG. 2 for printed circuit trace 8' of reference electrode 8.

What is claimed is:

1. A gas sensor, comprising:
   a body configured as a sintered ceramic laminate;
   a reference air duct arranged within a layer of the laminate;
   an electrical resistance heater arranged on a first side of the reference air duct;
   an electrode arrangement arranged on a second side of the reference air duct, the electrode arrangement including at least one internal reference electrode arranged on a border wall of the reference air duct and at least regionally permeable to gas and a Nernst electrode configured to be acted upon by the gas to be sensed and at least regionally permeable to gas, the Nernst electrode separated from the reference electrode by a solid electrolyte layer conductive and permeable to ions; and
   reference and Nernst electrode printed circuit traces connected to the respective electrodes, the printed circuit traces extending essentially in parallel to the reference air duct and, in a top view of layer planes of the laminate, the reference electrode printed circuit trace arranged at least partially next to the reference air duct,
   wherein the printed circuit traces connected to the electrodes have increased electrical conductivity with respect to the electrodes.

2. The gas sensor according to claim 1, further comprising:
   a separate chamber, the Nernst electrode arranged in the separate chamber;
   a diffusion path arranged in the body, the Nernst electrode configured to communicate with an exhaust gas stream via the diffusion path;
   an external pump electrode directly exposed to the exhaust-gas stream;
   an internal pump electrode arranged within the separate chamber and configured to cooperate via the solid electrolyte layer with the external pump electrode; and
   wherein, in a top view of the layer planes of the laminate, at least one of the Nernst electrode, the internal pump electrode, and the external pump electrode extends beyond borders of the chamber.

3. The gas sensor according to claim 2, further including an exhaust gas annular space, wherein outside of the chamber, in a top view, at least one of the Nernst electrode, the internal pump electrode and the external pump electrode has a large-area region that extends beyond the exhaust gas annular space in a direction of an exhaust-side, top end of the body.

4. The gas sensor according to claim 1, wherein the gas sensor is configured as a lambda probe.

5. The gas sensor according to claim 1, wherein the electrolyte layer is conductive and permeable to oxygen ions.

6. The gas sensor according to claim 1, wherein the reference electrode printed circuit trace runs alongside the reference air duct.

7. A gas sensor, comprising:
   a body configured as a sintered ceramic laminate;
   a reference air duct arranged within a layer of the laminate;
   an electrical resistance heater arranged on a first side of the reference air duct;
   an electrode arrangement arranged on a second side of the reference air duct, the electrode arrangement including at least one internal reference electrode arranged on a border wall of the reference air duct and at least regionally permeable to gas and a Nernst electrode configured to be acted upon by the gas to be sensed and at least regionally permeable to gas, the Nernst electrode separated from the reference electrode by a solid electrolyte layer conductive and permeable to ions;
   reference and Nernst electrode printed circuit traces connected to the electrodes, the printed circuit traces extending essentially in parallel to the reference air duct and, in a top view of layer planes of the laminate, the reference electrode printed circuit trace arranged at least partially next to the reference air duct;
   a separate chamber, the Nernst electrode arranged in the separate chamber;
   a diffusion path arranged in the body, the Nernst electrode configured to communicate with an exhaust gas stream via the diffusion path;
   an external pump electrode directly exposed to the exhaust-gas stream; and
   an internal pump electrode arranged within the separate chamber and configured to cooperate via a second solid electrolyte layer with the external pump electrode;
   wherein, in a top view of the layer planes of the laminate, a portion of at least one of the Nernst electrode, the internal pump electrode, and the external pump electrode extends beyond borders of the chamber, the portion excluding circuit traces of the at least one of the Nernst electrode, the internal pump electrode, and the external pump electrode.

8. The gas sensor according to claim 7, wherein the printed circuit traces connected to the electrodes have increased electrical conductivity with respect to the electrodes.

9. The gas sensor according to claim 8, wherein the printed circuit traces have one of an increased metal and increased platinum content with respect to the electrodes.

10. The gas sensor according to claim 9, wherein the gas sensor is configured as a lambda probe.

11. The gas sensor according to claim 9, wherein the electrolyte layer is conductive and permeable to oxygen ions.

12. The gas sensor according claim 8, wherein the printed circuit traces are configured with an increased thickness with respect to the electrodes.

13. The gas sensor according to claim 12, wherein the gas sensor is configured as a lambda probe.

14. The gas sensor according to claim 12, wherein the electrolyte layer is conductive and permeable to oxygen ions.

15. The gas sensor according to claim 8, wherein the printed circuit traces are formed as a double layer.

16. The gas sensor according to claim 15, wherein the gas sensor is configured as a lambda probe.

17. The gas sensor according to claim 15, wherein the electrolyte layer is conductive and permeable to oxygen ions.

18. The gas sensor according to claim 7, wherein the gas sensor is configured as a lambda probe.

19. The sensor according to claim 7, wherein the electrolyte layer is conductive and permeable to oxygen ions.

* * * * *

UNITED STATES PATENT AND TRADEMARK OFFICE
CERTIFICATE OF CORRECTION

PATENT NO. : 6,746,585 B2
DATED : June 8, 2004
INVENTOR(S) : Heiner Scheer et al.

It is certified that error appears in the above-identified patent and that said Letters Patent is hereby corrected as shown below:

Column 1,
Line 12, change "electrode that:is arranged" to -- electrode that is arranged --
Line 42, change "deficiency of oxygen ($\lambda>1$)." to -- deficiency of oxygen ($\lambda<1$). --

Signed and Sealed this

Twenty-sixth Day of April, 2005

JON W. DUDAS
*Director of the United States Patent and Trademark Office*